US010232086B2

(12) United States Patent
Cruz

(10) Patent No.: US 10,232,086 B2
(45) Date of Patent: Mar. 19, 2019

(54) THREE-DIMENSIONAL POROUS BIODEGRADABLE CELL SCAFFOLD

(75) Inventor: Carlos A Cruz, Holland, PA (US)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 1018 days.

(21) Appl. No.: 14/124,585

(22) PCT Filed: Nov. 16, 2011

(86) PCT No.: PCT/US2011/060969
§ 371 (c)(1),
(2), (4) Date: Dec. 6, 2013

(87) PCT Pub. No.: WO2013/074099
PCT Pub. Date: May 23, 2013

(65) Prior Publication Data
US 2014/0120062 A1 May 1, 2014

(51) Int. Cl.
A61L 27/48 (2006.01)
A61L 27/54 (2006.01)
A61L 27/56 (2006.01)
A61K 47/34 (2017.01)
C08L 29/04 (2006.01)
C08L 67/04 (2006.01)

(52) U.S. Cl.
CPC ............ A61L 27/48 (2013.01); A61K 47/34 (2013.01); A61L 27/54 (2013.01); A61L 27/56 (2013.01); C08L 29/04 (2013.01); C08L 67/04 (2013.01); C08L 2205/16 (2013.01)

(58) Field of Classification Search
None
See application file for complete search history.

(56) References Cited

U.S. PATENT DOCUMENTS

| 5,487,897 | A | * | 1/1996 | Polson | A61K 9/0024 424/425 |
| 5,711,960 | A | | 1/1998 | Shikinami | |
| 6,020,425 | A | * | 2/2000 | Wang | C08J 5/18 428/411.1 |
| 6,303,136 | B1 | | 10/2001 | Li et al. | |
| 6,348,069 | B1 | | 2/2002 | Vacanti et al. | |
| 6,638,312 | B2 | | 10/2003 | Plouhar et al. | |
| 7,425,288 | B2 | | 9/2008 | Flodin et al. | |
| 2007/0041952 | A1 | | 2/2007 | Guilak et al. | |
| 2011/0045047 | A1 | * | 2/2011 | Bennett | A61L 27/24 424/422 |
| 2012/0040015 | A1 | * | 2/2012 | Lehtonen | A61L 27/446 424/602 |

FOREIGN PATENT DOCUMENTS

JP 10-298108 11/1998
JP 2007-063516 3/2007

OTHER PUBLICATIONS

Machine translation of JPH10298108, Kakizawa et al., Nov. 1998.*
(Continued)

Primary Examiner — Shawn Mckinnon

(57) ABSTRACT

Disclosed are composites comprising water-soluble polymeric fibers dispersed in a biodegradable polymer matrix, as well as methods of making and using such composites.

26 Claims, 6 Drawing Sheets

(56) References Cited

OTHER PUBLICATIONS

Wikipedia, https://en.wikipedia.org/wiki/Polyvinyl_alcohol, page visited on Oct. 30, 2016.*
Celanese Acetate, Complete Textile Glossary, 2001.*
Kawazoe et al. ("Three-dimensional Cultures of Rat Pancreatic RIN-5F Cells in Porous PLGA-collagenHybrid Scaffolds", Journal of Bioactive and Compactible Polymers, vol. 24, Jan. 2009, pp. 25-42 (Year: 2009).*
Badiger, et al., "Porogens in the Preparation of Microporous Hydrogels based on Poly(Ethylene Oxides)," Biomaterials, vol. 14, Issue 14, Nov. 1993, pp. 1059-1063.
"Biofelt," Biomedical Structures, Accessed at http://www.bmsri.com/biofelt/ on Nov. 19, 2013 (1 page).
Ghosh, S., et al., "The Double Porogen Approach as a New Technique for the Fabrication of Interconnected Poly(L-Lactic Acid) and Starch Based Biodegradable Scaffolds," J Mater Sci: Mater Med (2007), 18: 185-193.
Han, et al., "Projection Microfabrication of Three-Dimensional Scaffolds for Tissue Engineering," Journal of Manufacturing Science and Engineering, 130, 021005-1-4 (2008).
Hsieh, et al., "Nano-Porous Ultra-High Specific Surface Fibers," National Textile Center Research Briefs—Chemistry Competency: Jun. 2004.
Hubbell, J.A., "Polymers in Tissue Engineering," Ch. 18 in Macromolecular Engineering: Precise Synthesis, Materials Properties, Applications, pp. 2719-2742, (2007).
International Search Report and Written Opinion in PCT/US2011/060969 dated Feb. 15, 2012.
Kuraray Kuralon and Kuralon K-II Product Information; Accessed at http://www.kuraray.us.com/products/fibers/kuralon-and-kuralon-k-ii/ on Sep. 16, 2013 (3 pages).
Langer, R. et al, "Tissue Engineering," Science, 260, 920-926, (1993).
Mihai, et al., "Rheology and Extrusion Foaming of Chain-Branched Poly(lactic acid)," Polym. Eng. Sci., 50: 629-642, (2010).
Moroni, et al., "3D Fiber Deposited Scaffolds for Tissue Engineering: Influence of Pores Geometry and Architecture on Dynamic Mechanical Properties," Biomaterials, vol. 27, Issue 7, Mar. 2006, pp. 974-985.
Phipps M.C., et al., "Increasing the Pore Sizes of Bone-Mimetic Electrospun Scaffolds Comprised of Polycaprolactone, Collagen I and Hydroxyapatite to Enhance Cell Infiltration," Biomaterials, 2012, vol. 33, pp. 524-534.
Sawalha, et al., "Addition of Oils to Polylactide Casting Solutions as a Tool to Tune Film Morphology and Mechanical Properties," Polym. Eng. Sci., 50: 513-519, (2010).
"Poly(lactide-co-glycolide) copolymer (PLGA)," Society for Biomaterials: Biomaterials of the Month, Sep. 2008, Accessed at http://www.biomaterials.org/week/bio25.cfm.
"STAR Biomaterials," Society for Biomaterials: Biomaterials of the Month, Sep. 2009, Accessed at http://www.biomaterials.org/week/bio35.cfm.
Traverse, E., et al., "3D Polymeric Scaffolds for Soft Tissue Engineering," NAST Centre, Accessed at http://www.centronast.com/archives/193.

* cited by examiner

THREE-DIMENSIONAL POROUS BIODEGRADABLE CELL SCAFFOLD

CROSS-REFERENCE TO RELATED APPLICATIONS

The present application is the U.S. national stage application of International Application No. PCT/US2011/060969, filed on Nov. 16, 2011, the entire contents of which are incorporated herein by reference in their entirety.

TECHNICAL FIELD

The present technology relates generally to composited for highly porous matrices or scaffolds. In particular, the present technology relates to the field of composites used for three-dimensional porous biodegradable scaffolds capable of being used as biological substitutes in tissue engineering and drug delivery systems.

BACKGROUND

The following description is provided to assist the understanding of the reader. None of the information provided or references cited is admitted to be prior art to the present technology.

Highly porous three-dimensional biodegradable composites are useful for tissue engineering scaffolds and drug delivery systems, among other things. Two key parameters in the design of this type of composite material are the size associated with the pores and their interconnectivity. A minimum size of about 10 µm is recommended to allow cell motion into the scaffold. Numerous methods have been proposed to produce suitable scaffolds from a variety of composite materials and include techniques that range from using nonwoven textiles to microfabrication. Some of the newest techniques have gained in sophistication and control, but they require highly specialized equipment and personnel. While progress has been made in producing composite materials for fabricating porous scaffolds, simple, current solutions ideally find a compromise between meeting the standards with respect to size and interconnectivity and ease and cost of production and, therefore, often fail to optimize either attribute. Therefore, it is desirable to pursue economical methods using conventional, readily available equipment which produces composites having well-defined pores of desired size and connectivity.

SUMMARY

The present technology provides the use of a water soluble fiber that can be dispersed in a molten polymer to produce a base composite. The composite is treated with water afterwards and the fiber dissolved, leaving behind hollow pores of dimensions that correspond to those of the original fiber. The fibers may be in the form of a woven or non-woven textile before being placed in the matrix, thus allowing for the formation of a three-dimensional network. The preformed nature of the fiber therefore influences the diameter and length of the pores in the scaffold.

In accordance with one aspect, the present technology provides a composite which includes water-soluble polymeric fibers dispersed in a biodegradable polymer matrix such that a majority of the fibers are in contact with other fibers and a plurality of the fibers contact a surface of the matrix.

In some embodiments, the water-soluble polymeric fibers include poly(vinyl alcohol), poly(vinyl pyrrolidone) or polyethylene oxide. In some embodiments, the water-soluble fibers include poly(vinyl alcohol) having medium or low degree of hydrolysis. In some embodiments, the poly (vinyl alcohol) of the water-soluble poly(vinyl alcohol) fibers have a weight average molecular weight of about 26,000 to about 36,000.

In some embodiments, the water-soluble polymeric fibers are at least 95% soluble when 1 gram of fiber is kept in 100 mL of water, for at least 30 minutes at a temperature of about 60° C.

In some embodiments, the water-soluble poly(vinyl alcohol) fibers have a melting point which is above the melt-processing temperature or the extrusion temperature used during preparation of the composite. In some embodiments, the water-soluble polymeric fibers have an average diameter of about 0.1 µm to about 200 µm. In other embodiments, the water-soluble polymeric fibers have an average diameter of about 1 µm to about 50 µm. In some embodiments, the water-soluble polymeric fibers have a length greater than their diameter. In some embodiments, the water-soluble polymeric fibers have an average length greater than 0.05 mm.

In some embodiments, the water-soluble polymeric fibers are arranged in a woven or non-woven pattern. In some embodiments, the non-woven pattern is a felt. In some embodiments, the water-soluble polymeric fibers include about 30 wt % to about 75 wt % of the total weight of the composite.

In some embodiments, the biodegradable polymer matrix includes poly(lactic acid), poly(glycolic acid), poly(caprolactone), poly(lactic acid) copolymer, poly(glycolic acid) copolymer, poly(caprolactone) copolymer, or a mixture of any two or more thereof.

In some embodiments, the composite further includes a water-soluble polymeric additive that is immiscible with the matrix polymer. In some embodiments, the water-soluble polymeric additive is polyethylene glycol, polyethylene oxide, polyvinylpyrrolidone, or poly(2-ethyl-2-oxazoline).

In another embodiment, the composite further includes a water-soluble non-polymeric additive that is immiscible with the matrix polymer. In some embodiments, the water-soluble non-polymeric additive is selected from the group consisting of sodium chloride, calcium chloride, magnesium chloride, magnesium sulfate, potassium sulfate, potassium chloride, sodium sulfate, sodium acetate, ammonium phosphate, ammonium sulfate, sucrose, glucose, fructose, and combinations thereof.

In one aspect, a composite is provided including water-soluble poly(vinyl alcohol) fibers dispersed in a biodegradable polymer matrix such that a majority of the fibers are in contact with other fibers and a plurality of the fibers contact a surface of the matrix.

According to another aspect, a method of making the biodegradable polymer matrix is provided. In one embodiment, the method includes melt-processing a biodegradable polymer and water-soluble poly(vinyl alcohol) fibers to provide a composite in which the fibers are dispersed throughout a matrix formed by the biodegradable polymer such that a majority of the fibers are in contact with other fibers and a plurality of the fibers contact a surface of the matrix.

In some embodiments, the melt-processing is carried out at a temperature of about 40° C. to about 200° C.

In some embodiments, the poly(vinyl alcohol) fibers, biodegradable polymer and one or more of water-soluble additives which are immiscible in the biodegradable polymer are processed together in a batch melt mixer and are compression-molded or extruded as a film, a sheet, a yarn, a cylindrical strand or strands, a tube, or a sheet or film having a cylindrical shape.

In some embodiments, the poly(vinyl alcohol) fibers, biodegradable polymer and one or more of water-soluble additives which are immiscible in the biodegradable polymer are combined in an extruder and the resulting composite is extruded as a film, a sheet, a yarn, a cylindrical strand or strands, a tube, or a sheet or film having a cylindrical shape.

In some embodiments, the poly(vinyl alcohol) fibers are first formed into a woven or non-woven construct and the biodegradable polymer matrix is deposited on to the construct and subsequently melted, compressed and cooled to form a film, a sheet, a yarn, a cylindrical strand or strands, a tube, or a sheet or film having a cylindrical shape.

In some embodiments, the poly(vinyl alcohol) fibers are first formed into a woven or non-woven construct and placed in a mold, the biodegradable polymer is injected into the mold and the injection-molded composite is subsequently cooled to form a film, a sheet, a yarn, a cylindrical strand or strands, a tube, or a sheet or film having a cylindrical shape.

In another aspect, a method of making the composite is provided. In some embodiments, the method includes exposing a composite to water or an aqueous solution under continuous agitation for a time and at a temperature sufficient to provide a porous biodegradable polymer matrix. In some embodiments, the composite includes a water-soluble poly(vinyl alcohol) fiber dispersed in a biodegradable polymer matrix such that a majority of the fibers are in contact with other fibers and a plurality of the fibers contact a surface of the matrix.

In some embodiments, the temperature of the water or aqueous solution is about 30° C. to about 60° C.

In some embodiments, the method further includes coating a surface of the porous biodegradable polymer matrix with a hydrophilic polymer. In some embodiments, the hydrophilic polymer is selected from the group consisting of fibronectin, vitronectin, laminin, collagen, elastin, and combinations thereof.

In one aspect, a porous biodegradable polymer matrix having tubular-like channels and an interconnected porous network is provided. In one embodiment, the porous biodegradable polymer matrix is formed by methods of the present technology. In some embodiments, the porous biodegradable polymer matrix has pores with diameters of about 10 µm to about 200 µm. In some embodiments, the porous biodegradable polymer matrix includes cells entrained therein.

In another aspect, a method which includes implanting a porous biodegradable polymer matrix of the present technology, into a subject in need thereof, is provided.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

Figure 1:
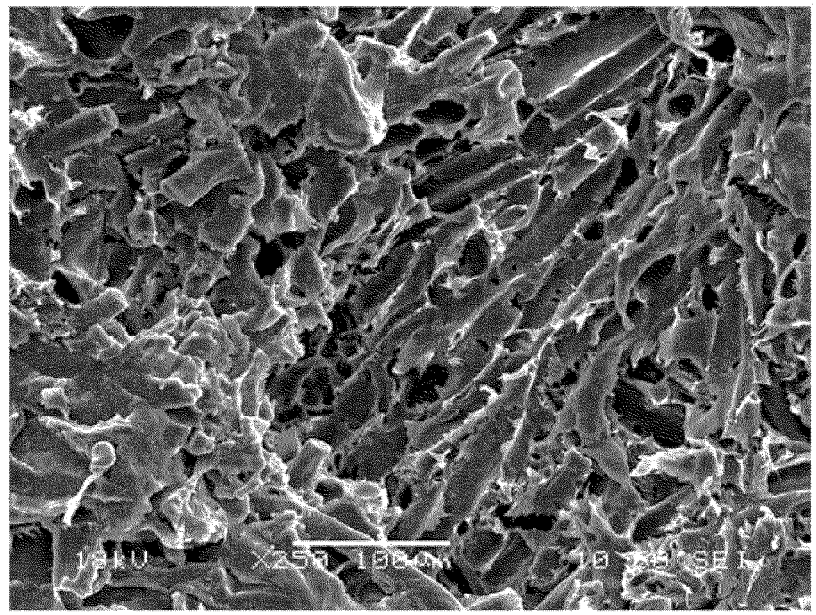
FIG. 1 shows a scanning electron microscope (SEM) image of an illustrative embodiment of a composite of the present technology, which includes poly(caprolactone) (PCL)/poly(ethylene oxide) (PEO)/poly(vinyl alcohol) (PVA) fibers in a weight ratio of 40/15/45, after extraction at 40° C.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The technology is described herein using several definitions, as set forth throughout the specification.

For the purposes of this disclosure and unless otherwise specified, "a" or "an" means "one or more."

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The embodiments, illustratively described herein, may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described, or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specifically specified.

As used herein, the term "and/or" shall also be interpreted to be inclusive in that the term shall mean both "and" and "or." In situations where "and/or" or "or" are used as a conjunction for a group of three or more items, the group should be interpreted to include one item alone, all of the items together, or any combination or number of the items.

Polymers useful in the present technology include those known to be suitable for use in vivo, e.g., in tissue engineering, and will be readily apparent to one skilled in the art. Because the polymeric matrices are used in vivo, biocompatibility of the polymers used is desired. As used herein, "biocompatible" refers to a material that is compatible with the host in which the material is implanted. In some cases, it may be desirable that after new tissue has grown on the polymeric matrices, that the polymeric matrix is expelled by a body in which it is implanted. Therefore, in some embodiments, the polymers to be used may be bioabsorbable or biodegradable. As used herein, "bioabsorbable" refers to the absorption of the material by a host in which the material is implanted. As used herein, "biodegradable" refers to the ability of a material to be absorbed or eroded in the host in which the material is implanted either by chemical or physical means. In some embodiments, the polymers are bioabsorbable.

As used herein, the term "composite" indicates materials consisting of two or more constituents (phases) that are combined at the macroscopic level and are not soluble in each other. As used herein, the term "matrix" denotes the physical structure of the polymer. In this sense the matrix functions as a three-dimensional structural template or support for colonization by cells or tissues or for delivery of drugs.

Disclosed herein are highly porous, three-dimensional (3D) biodegradable structures useful for scaffold manufacturing. This disclosure is drawn, among other things, to composites comprising water-soluble polymeric fibers dispersed in a biodegradable polymer matrix. In one aspect, the composites can be used to prepare highly interconnected 3D porous structures which can be used in a variety of applications including as tissue scaffolds and in drug delivery systems. The composites and methods of present technology provide a cost-effective, efficient way for providing 3D porous structures with tubular-like channels having improved intercommunication between porous regions and a homogenous structure.

Thus, in one aspect, the present disclosure provides a composite comprising water-soluble polymeric fibers dispersed in a biodegradable polymer matrix such that a majority of the fibers are in contact with the other fibers and a plurality of the fibers contact a surface of the matrix.

Polymer fibers useful in the present technology include those known to be soluble in water or even in water-organic solvent mixtures. Suitable polymer materials for fibers include those which retain their shape through mild melt processing and can be selectively dissolved and removed after forming the composite. Examples of the water-soluble polymeric fibers include poly(vinyl alcohol) (PVA), polyethylene glycol, poly(vinylpyrrolidone) (PVP), poly(ethyl oxazaline) (PEOX), hydroxypropymethylcellulose (HPMC), poly(ethylene oxide) (PEO), polyacrylic acid (PAAc), Poly(N-vinylpyrrolidone) (PNVP) and polyacrylamide (PAM). Other types of polymeric fibers useful in the present technology include fibers which are soluble in water-solvent mixtures, such as, e.g., ethyl vinyl alcohol (a copolymer of ethylene and vinyl alcohol), which is soluble in isopropanol-water mixture.

In one embodiment, the water soluble polymeric fibers include poly(vinyl alcohol) fibers. In some embodiments, the water-soluble fibers include poly(vinyl alcohol) having medium or low degree of hydrolysis.

The polymeric fibers are characterized by having good solubility in water. In some embodiments, the water-soluble polymeric fibers have a solubility of at least 1 g/L in water having a temperature of about 60° C. In other embodiments, the water-soluble poly(vinyl alcohol) fibers have a solubility of at least 5 g/L in water having a temperature of about 60° C. In other embodiments, the water-soluble polymeric fibers have a solubility of at least 10 g/L in water having a temperature of about 60° C. Examples of the water solubility of the polymeric fibers include at least 50% soluble, at least 55% soluble, at least 60% soluble, at least 65% soluble, at least 70% soluble, at least 75% soluble, at least 80% soluble, at least 90% soluble, at least 95% soluble, or ranges between and including any two of these values, when 1 gram of fiber is kept in 100 ml of water, for at least 30 minutes at a temperature of about 60° C. In some embodiments, the water-soluble polymeric fibers are poly(vinyl alcohol) fibers which are at least 95% soluble when 1 gram of fiber is kept in 100 ml of water for at least 30 minutes at a temperature of about 60° C. (i.e., has a solubility of at least 9.5 g/L at these conditions).

The composites of the present technology can be prepared by several methods known in the art. Examples of such methods include melt-processing, extrusion, injection molding, etc. In some embodiments, the composites are prepared using melt-processing or an extrusion process. Accordingly, in some embodiments, the water-soluble polymeric fibers have a melting point which is above the melt-processing temperature or the extrusion temperature used during preparation of the composite. In one embodiment, the water soluble polymeric fibers include PVA fibers. In some embodiments, the melting point of the PVA fibers is about 150° C. to about 300° C. In some embodiments, the melting point of the PVA fibers is about 180° C. to about 250° C. In some embodiments, the melting point of the PVA fibers is about 200° C. to about 230° C. Examples of melting points of the PVA fibers include about 150° C., about 160° C., about 170° C., about 180° C., about 180° C., about 190° C., about 200° C., about 210° C., about 220° C., about 230° C., about 240° C., about 250° C., about 260° C., about 270° C., about 280° C., about 290° C., about 300° C., and ranges between and including any two of these values.

In some embodiments, the poly(vinyl alcohol) of the water-soluble poly(vinyl alcohol) fibers has a weight average molecular weight of about 10,000 to about 25,000, about 25,000 to about 40,000, about 40,000 to about 55,000, about 55,000 to about 70,000, about 70,000 to about 85,000, about 85,000 to about 100,000 or about 100,000 to about 115,000 or higher. In some embodiments, the poly(vinyl alcohol) of the water-soluble poly(vinyl alcohol) fibers has a weight average molecular weight of about 26,000 to about 36,000. Examples of molecular weights of the water-soluble PVA fibers include about 25,000, about 30,000, about 35,000, about 40,000, about 45,000, about 50,000, about 55,000, about 60,000, about 65,000, about 70,000, about 75,000, about 80,000, about 85,000, about 90,000, about 95,000, about 100,000, about 105,000, about 110,000, about 115,000, and ranges between and including any two of these values.

The preformed nature of the fibers dictates the diameter and length of the final pores of the composite. Therefore, the length and the diameter of the polymeric fibers can be suitably optimized to obtain the desired porosity and interconnectivity of the scaffold matrix. Thus, in some embodiments, the composites include water-soluble poly(vinyl alcohol) fibers having an average diameter of about 1 µm to about 500 µm, about 3 µm to about 300 µm, about 5 µm to about 200 µm, about 10 µm to about 50 µm, or about 10 µm to about 30 µm. In some embodiments, the water-soluble poly(vinyl alcohol) fibers have an average diameter of about 10 µm to about 50 µm. In other embodiments, the water-soluble poly(vinyl alcohol) fibers have an average diameter of about 50 µm to about 200 µm. Examples of average diameter of the water-soluble poly(vinyl alcohol) fibers include about 10 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, and ranges between and including any two of these values. In some embodiments, all the water-soluble poly(vinyl alcohol) fibers may have a similar or identical average diameter. In other embodiments, fibers having two or more average diameters can be used. For example, a combination of fibers having a smaller diameter of about 10 µm to about 20 µm and fibers having larger diameter of about 90 µm to about 110 µm can be used.

Fibers of any length can be suitably used as long as they can be processed in the equipment used to prepare the composite structure. The length of the fibers can be adapted depending on the dimensions of the composite as well as the desired interconnectivity. For example, the length of the fibers can vary from about 0.01 mm to about 1 m. In some embodiments, the length of the fibers can vary from about 0.01 mm to about 100 mm. In some embodiments, the composites include water-soluble poly(vinyl alcohol) fibers have average length greater than their average diameter. Examples of the average length of the water-soluble poly(vinyl alcohol) fibers include about 0.001 mm, about 0.005 mm, about 0.01 mm, about 0.05 mm, about 0.1 mm, about 0.5 mm, about 1 mm, about 1.5 mm, about 2 mm, and ranges between and including any two of these values. In some embodiments, all the water-soluble poly(vinyl alcohol) fibers may have identical length. In other embodiments, fibers having two or more different lengths can be used.

The polymeric fibers useful in the present invention can be acquired commercially or prepared by methods known in the art such as, for example, electrospinning, meltspinning or melt-blowing. Commercially available fibers suitable for use in the present technology include, for example, the Kuralon® WN-2 or WN-4 type PVA fibers from Kuraray, Japan or the Mewlon® SPM type PVA fibers from Unitika Ltd., Japan.

In some embodiments, the water-soluble poly(vinyl alcohol) fibers are arranged in a woven or non-woven pattern. In some embodiments, the non-woven pattern is a felt. The felt can be produced using standard felting methods known in the art. In some embodiments, the felt is produced by spraying the fibers with a small amount of water at room temperature and then pressed down between heated rotating cylinders at a suitable temperature to produce fiber-fiber sintering.

The amount of fibers used in the composite can be varied to achieve the desired level of porosity and interconnectivity. In some embodiments, the water-soluble poly(vinyl alcohol) fibers make up about 1 wt % to about 99 wt % of the total weight of the composite. In some embodiments, the water-soluble poly(vinyl alcohol) fibers include about 10 wt % to about 80 wt % of the total weight of the composite. In other embodiments, the water-soluble poly(vinyl alcohol) fibers include about 30 wt % to about 75 wt % of the total weight of the composite. In yet other embodiments, the water-soluble poly(vinyl alcohol) fibers include about 40 wt % to about 60 wt % of the total weight of the composite. Examples of the total wt % of the composite that the water-soluble poly(vinyl alcohol) fibers make up include about 1 wt %, about 2 wt %, about 5 wt %, about 10 wt %, about 20 wt %, about 30 wt %, about 40 wt %, about 50 wt %, about 60 wt %, about 70 wt %, about 75 wt %, about 80 wt %, about 85 wt %, about 90 wt %, about 95 wt %, about 96 wt %, about 97 wt %, about 98 wt %, about 99 wt %, and ranges between and including any two of these values.

The polymer matrix may include suitable polymeric material known in the art. Typically, the matrix is not soluble in water or water-organic solvent mixtures under conditions which render the fibers soluble. Biodegradable and biocompatible polymers that may be used for the polymer matrix may include, but are not limited to, poly(lactic acid) (PLA), poly(glycolic acid) (PGA), and poly(caprolactone) (PCL), as well as poly(lactic acid) copolymer, poly(glycolic acid) copolymer, and poly(caprolactone) copolymer, or a mixture of any two or more thereof. Polymers such as PLA and PGA are generically known as polyhydroxyalkanoates. Other biodegradable polymers include materials such as poly(lactide-co-glycolide), polycarbonates, polyamides, polyanhydrides, polyamino acids, polyorthoesters, polyacetates, polycyanoacrylates, degradable polyurethanes, degradable polyesters, or co-polymers or blends of any two or more such polymers. In some embodiments, the matrix may include a bioabsorbable polymer such as poly (epsilon-caprolactone). These polymers may be used in various forms such as granules, powder, pellets, etc.

Various additives known in the art may optionally be added to enhance the properties of the biodegradable matrix. Suitable additives which selectively react with the matrix polymer, but not with the fiber polymer, may be added in suitable amounts to the matrix material. Examples of such additives include epoxy-functionalized additives such as CESA-Extend OMAN 698493 (from Clariant) or poly (propylene glycol) diglycidyl ether.

The composite may also further include at least one additive. These additives may serve to promote extraction and interconnectivity, decrease the amount of biodegradable matrix used, and increase scaffold porosity. In some embodiments, the composite may include a water-soluble polymeric additive. In some embodiments, the additive is immiscible with the matrix polymer. In some embodiments, the water-soluble polymeric additive is selected from polyethylene glycol (PEG), polyethylene oxide (PEO), polyvinylpyrrolidone (PVP), poly(2-ethyl-2-oxazoline), or combinations thereof. In some embodiments, the composite may further include a water-soluble non-polymeric additive that is immiscible with the matrix polymer. In some such embodiments, the water-soluble non-polymeric additive is selected from the group consisting of is sodium chloride, calcium chloride, magnesium chloride, magnesium sulfate, potassium sulfate, potassium chloride, sodium sulfate, sodium acetate, ammonium phosphate, ammonium sulfate, sucrose, glucose, fructose, and combinations thereof. In some embodiments, the composite may include about 1 wt % to about 40 wt % of water-soluble additive based on the total weight of the composite. In some embodiments, the composite may include about 5 wt % to about 30 wt % additive based on the total weight of the composite. In other embodiments, the composite may include about 10 wt % to about 20 wt % additive based on the total weight of the composite. Examples of the amount of water-soluble additive, based on the total weight of the composite include about 1 wt %, about 5 wt %, about 10 wt %, about 15 wt %, about 20 wt %, about 25 wt %, about 30 wt %, about 35 wt %, about 40 wt %, and ranges between and including any two of these values.

In another aspect, the present technology provides a method for preparing the composite. The method includes melt-processing a biodegradable polymer and water-soluble polymeric fibers to provide a composite in which the fibers are dispersed throughout a matrix formed by the biodegradable polymer, such that a majority of the fibers are in contact with other fibers and a plurality of the fibers contact a surface of the matrix. In some embodiments of the method, the polymeric fibers include poly(vinyl alcohol) fibers. In some embodiments, the biodegradable matrix polymer includes poly (epsilon-caprolactone).

The melt-processing may be conducted using commonly known methods such as melt-spinning, extrusion, blow molding or injection molding. The melt-processing may be conducted in a continuous or a batch mode. The molten mass of matrix polymer and fiber materials may be subsequently transferred into a mold, and pressed down into a plaque by applying pressure and temperature. In some embodiments, the poly(vinyl alcohol) fibers, biodegradable polymer and one or more of water-soluble additives, which are immiscible in the biodegradable polymer, are processed together in a batch melt mixer and are compression-molded or extruded. In other embodiments, the poly(vinyl alcohol) fibers, biodegradable polymer and one or more of water-soluble additives which are immiscible in the biodegradable polymer are combined in an extruder and the resulting composite is extruded. In another embodiment, the poly(vinyl alcohol) fibers are first formed into a woven or non-woven construct and the biodegradable polymer matrix is deposited on to the construct and subsequently melted, compressed and cooled. In yet another embodiment, the poly(vinyl alcohol) fibers are first formed into a woven or non-woven construct and placed in a mold, the biodegradable matrix is then injected in to the mold and injection-molded composite is subsequently cooled. In some embodiments, the fibers are first incorporated into the matrix, with or without suitable additives and the composition is then injection-molded into a desired shape.

The biodegradable matrix can be configured to be in any desired shape such as for example, a film, a sheet, a mesh, a pellet, a disk, a cord, a yarn, a cylindrical strand or strands, a tube, or a sheet or film having a cylindrical shape. In some embodiments, the biodegradable polymer matrix is extruded or molded in the form of a film, a sheet, a yarn, a cylindrical strand or strands, a tube, or a sheet or film having a cylindrical shape. The dimensions of the film, sheet, yarn or strand can be adjusted as desired by controlling the parameters of the molding or extrusion process.

In some embodiments, the extrusion can be conducted using a single-screw extruder or a twin-screw extruder. Suitable types of feeders such as, e.g., gravimetric feeders, or individual feeders for matrix and fibers, can be used to ensure that the fibers are well-dispersed in the matrix. The temperature of the extruders can be set appropriately to melt the polymer matrix material, while keeping the integrity of the fibers intact. The composite can be produced continuously as a sheet. Sheet thickness can be altered by modifying the feed rate, screw speed and sheet pulling rate.

In some embodiments, the polymer matrix material, fibers and additives can be simply dry-blended and subjected to compression molding at a suitable temperature. In other embodiments, pre-melting with shear in a plastograph closed chamber can be used to disperse short fibers into the matrix. The pre-melted mass can then be subjected to compression-molding to produce the desired composites that could be extracted. In one embodiment, the composite can then be subjected to extrusion to induce fiber dispersion and continually produce the composite. In some embodiments, extrusion methods can be used to induce fiber dispersion and continuously produce composite sheets.

In some embodiments, a larger scale batch mixing apparatus, such as for example a Banbury mixer, can also be used to produce large quantities of composite material. After pre-mixing the polymer matrix material, fibers and additives in a Banbury mixer, the composite can be subsequently extruded or subjected to compression-molding. Alternatively, the composite can be extruded and injection- or compression-molded.

In some embodiments, matrix foaming can be conducted simultaneously with fiber introduction. This can be done, for example, by introducing a foaming agent (porogen) along with the fibers, during the compounding step, without foaming. In some embodiments, the foaming step can be carried out after mixing the polymer and the fibers, under controlled conditions, and without having to deal with the intricacies of the foaming process during the mixing step.

In some embodiments, the fiber-matrix composited are prepared by melt-processing. In some embodiments, the melt-processing is conducted in a closed chamber. The melt-processing temperature may be suitably selected depending on the type and amount of matrix polymer and fiber polymer in the composite. In some embodiments, the temperature of the melt-processing is selected so that matrix polymer melts but the fibers do not. Thus, in some embodiments, the melt-processing is carried out at a temperature of about 10° C. to about 220° C. In some embodiments, the melt-processing is carried out at a temperature of about 40° C. to about 200° C. In some embodiments, the melt-processing is carried out at a temperature of about 80° C. to about 170° C. In some embodiments, the melt-processing is carried out at a temperature of about 90° C. to about 150° C. In some embodiments, the melt-processing is carried out at a temperature of about 100° C. to about 120° C. Examples of temperatures at which melt-processing is carried out include about 10° C., about 20° C., about 30° C., about 40° C., about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., about 200° C., about 210° C., about 220° C., and all ranges between and including these values.

Various additives, such as those mentioned above, may be added to facilitate melt-processing of the composite. In some embodiments, the additive may be a polymer such as poly(ethylene oxide). In other embodiments, the polymer may be a non-polymeric additive such as sugar or sodium chloride.

The concentration of the polymeric fibers in the composite may be altered depending on the desired porosity or interconnectivity in the composite. Examples of fiber concentration in the composite include at least about 10%, at least about 20%, at least about 30%, at least about 40%, at least about 50%, at least about 60%, at least about 70%, at least about 80% or at least about 90%, and ranges between and including these values. In some embodiments, the concentration of fibers in the composite may be at least about 55%.

After melt-processing the matrix and the fibers, the composite matrix may be subjected to suitable post-treatment methods. In some embodiments, the composite matrix may be subjected to solubilization and extraction to eliminate the fibers and produce a hollow interconnected network. In some embodiments, the method may include exposing the composite matrix to water or a water-solvent mixture under continuous agitation for a time and at a temperature sufficient to provide a porous biodegradable polymer matrix. In some embodiments, the exposing step may involve immersing the composite in water or water-solvent mixture.

The temperature of the water or aqueous solution may be such that it is sufficient to dissolve the polymeric fibers, but not the matrix. In some embodiments, the temperature of the water or aqueous solution is about 20° C. to about 100° C. In some embodiments, the temperature of the water or aqueous solution is about 25° C. to about 80° C. In some embodiments, the temperature of the water or aqueous solution is about 25° C. to about 70° C. In some embodiments, the temperature of the water or aqueous solution is about 30° C. to about 60° C. In some embodiments, the temperature of the water or aqueous solution is about 40° C. to about 50° C. Examples of the temperature of the water or aqueous solution include about 20° C., about 25° C., about 30° C., about 35° C., about 40° C., about 45° C., about 50° C., about 55° C., about 60° C., about 65° C., about 70° C., about 75° C., about 80° C., and ranges between and including any two of these values. Depending upon the amount of extractable materials, the extraction may be conducted over a suitable period of time such that substantially all of the fibers are dissolved and extracted. For example, at lower temperatures of about 25° C. to about 35° C., the extraction may take several days, but at temperatures of about 40° C. to about 50° C., the extraction may be completed within about 36 hours to about 50 hours. Typically, it was observed that temperatures above 40° C. increased the extraction rate. For example, about 50% of the soluble material can be extracted at 40° C. after 38 hours, whereas about 70% of extractable material is solubilized at 50° C. after 38 hours. In contrast, only a negligible amount of material can be extracted at 25° C. or lower temperatures. In some embodiments, the extraction process may be supplemented by using ultrasound to produce additional extraction. Thus, in some embodiments, the composites may be treated with water in an ultrasound bath during or after the extraction.

After solubilization and extraction, the extracted matrix may be dried suitably to form a biodegradable matrix which has a porous, three-dimensional, highly interconnected network of long, hollow cylinders. Thus, the present technology makes use of readily available materials and conventional melt-processing equipment to produce highly porous three-dimensional scaffolds wherein the dimensions of the pores are well-controlled due to the use of fibers as templates. The composites or matrix materials prepared using the present technology have design flexibility in terms of the materials used, permit control over micro and macro structure, processability and mechanical properties. A unique morphology that consists of well-defined channels results as a consequence of using the fiber template of the present technology. This is advantageous over methods using polymer granules or particles which would form irregular, disconnected pores.

The composites may be characterized through a variety of techniques. Such techniques include, but are not limited to, scanning electron microscopy (SEM), differential scanning calorimetry (DSC), transmission electron microscopy (TEM), atomic force microscopy (AFM), voltage-vs-current characteristics (V-I), thermogravimetric analysis (TGA), X-ray diffraction (XRD) studies, and energy dispersive X-ray analysis (EDAX). Various techniques known in the art can be used to determine that an interconnected porous network exists. For example, weight loss measurements, as well as scanning electron microscopy (SEM), porosity measurements and electrical resistance, can be used to determine the morphology of the composite.

Figure 2:
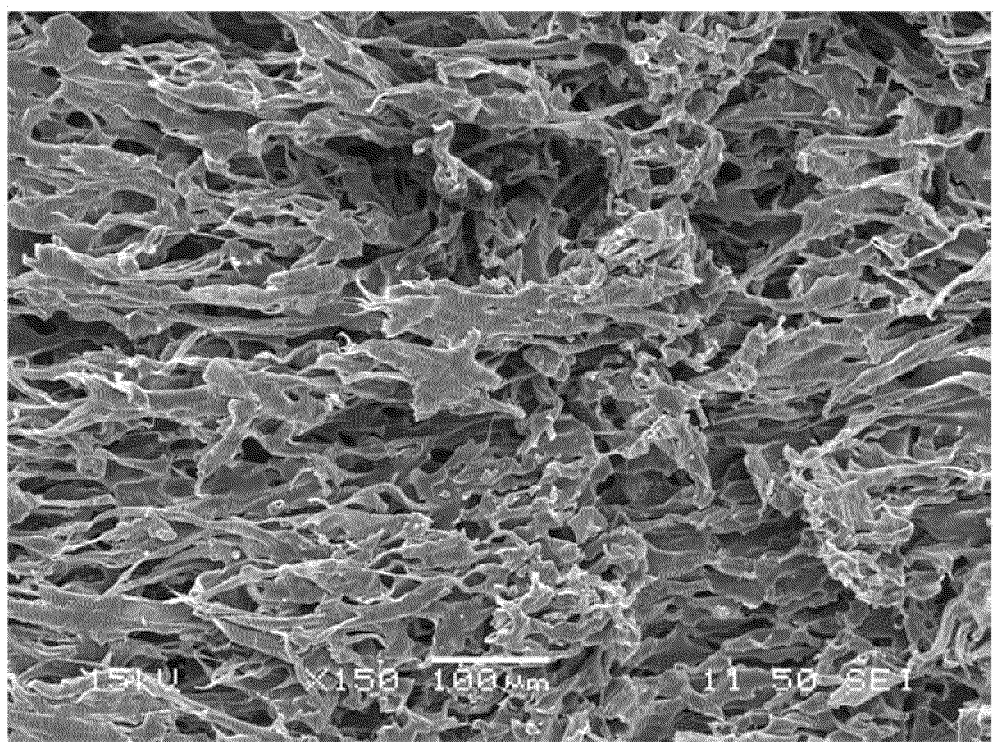
FIG. 2 shows an SEM image of an illustrative embodiment of a composite of the present technology, which includes PCL/PVA fibers in a weight ratio of 40/60, after extraction at 50° C.
Figure 3:
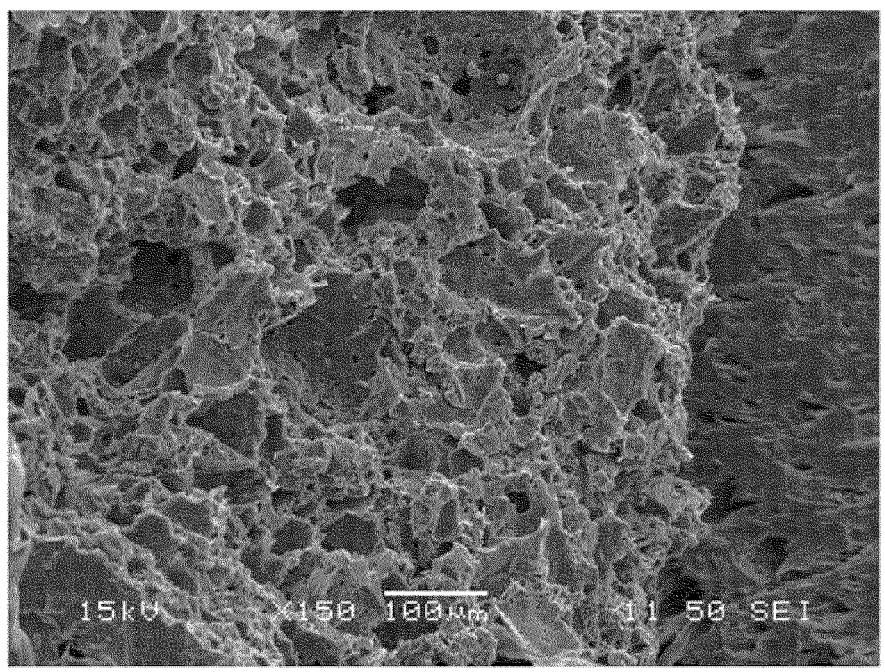
FIG. 3 shows an SEM image of a comparative example that is a composite, which includes PCL/Sugar in a weight ratio of 40/60, after extraction at 50° C.

With reference to FIG. 1, an SEM image of composite of present technology, which includes PCL/PEO/PVA (WN-4) fibers in a ratio of 40/15/45, after extraction at 40° C., is shown in accordance with an illustrative embodiment. The channel-like configuration of the composite is clearly visible. The porosity of the sample was determined to be about 50.7%. In contrast, FIG. 2 shows an SEM image of a sample of composite which includes PCL/Sugar in a ratio of 40/60, after extraction at 50° C. The composite shows sphere-like openings instead of channels and a porosity of about 44.9%. FIG. 3 shows an SEM image of a sample of composite of present technology, which includes PCL/Sugar/PVA (WN-4) fibers in a ratio of 40/10/50, after extraction at 50° C. The channel-like configuration is clearly visible. The porosity of this sample was determined to be 59.3%. It is clear from the figures that the composites of the present technology possess a three-dimensional porous structure consisting of well-defined channels and an improved porosity.

The composites and matrix materials of the present technology can be tuned for specific applications by modifying the amount and type of materials used, the processing conditions or other parameters. For example, the composites or matrix materials can be tailored using a variety of known post-treatment methods, giving them a flexibility to be used in several applications. Moreover, owing to their excellent biocompatibility and biodegradability, these composites and matrix materials can also be used for a wide variety of biomedical applications such as tissue engineering, drug and gene delivery, implants, prosthetic devices, vascular grafts, biosensors and artificial organs. For tissue engineering applications, the composites and matrix materials of the present technology can be modulated to closely mimic the biomedical properties of the tissues to be regenerated. Many other applications will be readily envisioned by those of skill in the art.

In view of some of the applications disclosed above, the hollow channels of the matrix may optionally be surface-coated with suitable materials to foster the adhesion and growth of cells, proteins and growth factors. Thus, in one embodiment, the method further includes coating the surface of the porous biodegradable polymer matrix with a hydrophilic polymer. Any suitable hydrophilic polymer known in the art may be used as a coating material. Examples of such hydrophilic polymer include fibronectin, laminin, vitronectin, thrombospondin, heparin, collagen, gelatin, elastin, fibrin, phosphatidylcholine, phosphatidylserine, phosphatidylethanolamine, sphingomyelin, derivatives thereof, and combinations thereof. In some embodiments, the hydrophilic polymer is selected from the group consisting of fibronectin, vitronectin, laminin, collagen, elastin, and combinations thereof.

In one aspect, the present technology provides a porous biodegradable polymer matrix formed by the methods described above. The biodegradable polymer matrix has pores with average diameter of about 1 μm to about 1000 μm, about 5 μm to about 500 μm, about 10 μm to about 200 μm, about 20 μm to about 100 μm, about 50 μm to about 80 μm, or about 60 μm to about 70 μm. Examples of average diameter of pores of the biodegradable polymer matrix include about 1 μm, about 5 μm, about 10 μm, about 20 μm, about 30 μm, about 40 μm, about 50 μm, about 60 μm, about 70 μm, about 80 μm, about 90 μm, about 100 μm, about 200 μm, about 300 μm, about 400 μm, about 500 μm, about 600 μm, about 700 μm, about 800 μm, about 900 μm, about 1000 μm, and ranges between and including any two of these values. The porous biodegradable polymer matrix formed by the present methods exhibit improved properties such as better intercommunication of porous regions, overall homogeneity, easier cell placement and smoother transport of nutrients or other substances. Conversely, in systems where only spherical-like pores are present, may of the pores are isolated with little or no intercommunication with the rest of the pores and the irregularity in the matrix may result in tortuous path for cell placement and transport of nutrients.

In some embodiments, the porous biodegradable polymer matrix further includes cells entrained therein. The matrices can be used to entrain various cells obtained from a wide variety of sources. It is possible to use any animal cell in the matrix of the present technology. The cells or tissues used may be mammalian, non-mammalian, vertebrate, or invertebrate in origin. For example, the cells or tissues may be derived from humans, non-human primates, mice, rats, dogs, horses, chickens, fish, hamster, guinea pig, reptiles, insects, and the like. These cells include progenitor cells which differentiate and proliferate to form cells having desired characteristics; stromal cells which relate to foundation supporting tissue; and mesenchymal cells which relate to connective tissues, blood and blood vessels, and other systems. Exemplary cells for use with the three-dimensional porous matrices include, but are not limited to, bone, osteoprogenitor cells, cartilage, muscle, liver, kidney, pancreas, skin, endothelial cells, gut or intestinal cells, or specialized cells such as cardiovascular cells (e.g., endocardial, myocardial and pericardial cells), cardiomyocytes, pulmonary or other lung cells, placental, amnionic, chorionic or foetal cells, stem cells, chondrocytes, embryonic cells, adult tissue, and stem cells.

The biodegradable, porous three-dimension matrix of the present technology may serve as a substrate upon which the biological cells may grow and propagate. In one aspect, the present technology provides a method which includes implanting the porous biodegradable polymer matrix into a subject in need thereof. In some embodiments, a plurality of matrices may be implanted into a patient's body. In some embodiments, the plurality of matrices may be interconnected by conduits before being placed in the subject's body. The biodegradable matrices of the present technology are not only environmentally responsive, but also tunable with respect to various properties, so that they impart both mechanical and chemical signals to entrained cells to foster the desired phenotypic expression and tissue development.

The term "patient" or "subject," as used herein includes any animal, that can benefit from use of the composites of the present technology. The subject can be a human or non-human. Thus, subjects includes mammals, e.g., a human, a primate, a dog, a cat, a horse, a cow, a pig, a goat or a rodent, e.g., a rat or mouse. In some embodiments, the subject is a human. The subjects may be normal, healthy subjects or subjects having, or at risk for developing, a particular biological disease or condition. By way of example only, the subject may be a subject in need of tissue repair, replacement or reconstruction.

The present technology, thus generally described, will be understood more readily by reference to the following examples, which are provided by way of illustration and are not intended to be limiting of the present technology.

EXAMPLES

Example 1

Standard Protocol for Producing Porous, Three-Dimensional Matrix 25 g of WN-4 fiber are cut in a Wiley mill and the fraction that passes a 20-mesh screen is collected. 20 g of cut WN-4 fiber, 15 g each of PCL and PEO are separately dried for 4 hours at 40° C. under vacuum. The dried components are then melt-blended in a Brabender Plasticorder bowl by first introducing PCL and PEO in the bowl and preheating the mixture at 90° C. and at rotor speed of 30 rpm. Once the polymers have melted, the fiber is gradually introduced in the bowl at an addition rate of about 1-2 g per minute. Once all the fiber has been added, the bowl is closed and the operation is continued for an additional minute. Higher rpm may be used for this last mixing step. The bowl is opened and its contents placed into a mold made up of a steel frame of the desired dimensions (e.g., 10×10 cm opening and 2 mm thickness) placed in between two steel plates that have been previously lubricated. The set is taken into a Carver press which is preheated to 150° C., where the polymers are first allowed to melt with no pressure applied. The platens of the press are then closed slowly and a pressure of 5000 lbs is applied for 4 min. The thermostat is then turned off and cooling water is let in through the system. The plaque is removed from the press.

The entire plaque, or a small portion of the plaque, can be used for further processing. If a specimen is to be prepared for testing, a specimen of the required dimensions (e.g., 1×1 cm) is cut from the sample produced. The specimen is held by a clip and immersed in water at 50° C. (250 cm³ water was used) with magnetic stirring. After 48 hours, the specimen is removed from the water and dried.

A variety of samples were prepared using the standard protocol described above, and varying the type and amount of polymers, fibers and additives, as well as the processing and extraction conditions, which are summarized in Tables 1-3 below:

TABLE 1

Water Extraction of various composites at 40° C.

| | Composition | | | | Preparation | | | Extraction | | |
|---|---|---|---|---|---|---|---|---|---|---|
| Sample No | PCL | PEO | SUGAR | FIBER (WN-4) | Brabender Premix | Molding Temp °C. | Molding Pressure $lb_f$ | Extraction at 40° C. wt % | Time hr | Surface Abrasion |
| 1 | 55 | 0 | 0 | 45 | Yes | 100 | 5000 | 2.4 | 90 | N |
| 2 | 40 | 15 | 0 | 45 | Yes | 100 | 5000 | 25.6 | 72 | Y |
| 3 | 40 | 0 | 15 | 45 | Yes | 100 | ≤700 | 26 | 72 | Y |
| 4 | 55 | 0 | 0 | 45 | No | 0 | ≤700 | | | |

TABLE 1-continued

Water Extraction of various composites at 40° C.

| | Composition | | | | Preparation | | | Extraction | | |
|---|---|---|---|---|---|---|---|---|---|---|
| Sample No | PCL | PEO | SUGAR | FIBER (WN-4) | Brabender Premix | Molding Temp ° C. | Molding Pressure lb$_f$ | Extraction at 40° C. wt % | Time hr | Surface Abrasion |
| 5 | 60 | 15 | 25 | — | Y | 100 | ≤700 | 12.8 | 83 | N |
| 6 | 30 | 30 | 40 | — | Y | 100 | ≤700 | 62.5 | 59 | N |
| 7 | 40$^a$ | 15 | 45 | | | | | 29.5 | 57 | |

$^a$An aqueous 1% solution of NaCl is prepared and 10 ml sprayed on 50 grams of PCL powder. The mixture is stirred and dried at 40° C. under vacuum to fully evaporate the water and produce fine salt crystallites. 20 g of this blend are blended with 30 g of sugar to produce the melt blend.

TABLE 2

Water Extraction of various composites at 50° C.

| | Composition | | | Preparation | | | Extraction | | |
|---|---|---|---|---|---|---|---|---|---|
| Sample No | PCL | SUGAR | FIBER (WN-4) | Brabender Premix | Molding Temp ° C. | Molding Pressure lb$_f$ | Extraction at 50° C. wt % | Time hr | Surface Abrasion |
| 8 | 40 | 20 | 40 | Y | 150 | 5000 | 47.7 | 48 | N |
| 9 | 40 | 60 | 0 | Y | 150 | 5000 | 57.9 | 48 | N |
| 10 | 40 | 10 | 50 | Y | 150 | 5000 | 52.2 | 48 | N |
| 11 | 50 | 10 | 40 | Y | 150 | 5000 | 25.7 | 48 | N |
| 12 | 40 | 15 | 45 | Y | 150 | 5000 | 57.1 | 48 | N |
| 13 | 40$^a$ | 60 | 0 | Y | 150 | 5000 | 57.2 | 48 | N |
| 14 | 40$^b$ | 60 | 0 | Y | 150 | 5000 | 59.0 | 48 | N |
| 15 | 40 | — | 60 | Y | 150 | 5000 | 53.8 | 48 | N |

$^a$An aqueous 1% solution of NaCl is prepared and 10 ml sprayed on 50 grams of PCL powder. The mixture is stirred and dried at 40° C. under vacuum to fully evaporate the water and produce fine salt crystallites. 20 g of this blend are blended with 30 g of sugar to produce the melt blend.
$^b$NaCl granules are added to PCL at a proportion of 1 to 100 and dry-blended together.

TABLE 3

Extraction of PLA extruded samples at 50° C. for 48 hours.

| | Composition Weight % | | | | | Extractables | |
|---|---|---|---|---|---|---|---|
| Sample No | PLA | PEO | WN-2 fibers | WN-4 fibers | Total, wt % | Remaining, Wt % | % Solubles Extracted |
| 16 | 70 | — | — | 30 | 70 | 69.8 | 0.3 |
| 17 | 60 | — | 40 | — | 40 | 38.8 | 3.0 |
| 18 | 40 | 20 | 40 | — | 60 | 38.9 | 35.2 |
| 19 | 50 | 10 | 40 | — | 50 | 46.7 | 6.6 |
| 20 | 50 | 25 | 25 | — | 50 | 37.6 | 24.8 |
| 21 | 60 | — | — | — | 40 | 20.0 | 50.0 |

The prepared samples were evaluated for their physical and structural characteristics such as volume, weight, density and porosity. Table 4 summarizes these characteristics for some of the samples.

TABLE 4

Measured dimensions, density and calculated porosity of composite samples.

| | Experimental conditions | | | Initial Dimensions | | | Final Dimensions | | | |
|---|---|---|---|---|---|---|---|---|---|---|
| Sample No. | Temp ° C. | Time h | % Extraction | Volume mm$^3$ | Weight g | Density g/cm$^3$ | Volume mm$^3$ | Weight g | Density g/cm' | Estimated Porosity % |
| 2 | 40 | 54 | 25.60 | 268 | 0.29 | 1.08 | 305 | 0.22 | 0.71 | 35.8 |
| 6 | 40 | 54 | 62.35 | 224 | 0.26 | 1.16 | 197 | 0.10 | 0.50 | 54.6 |
| 7 | 50 | 48 | 47.75 | 277 | 0.34 | 1.23 | 329 | 0.18 | 0.54 | 50.7 |
| 8 | 50 | 54 | 52.54 | 227.9 | 0.27 | 1.20 | 329 | 0.14 | 0.41 | 62.5 |
| 9 | 50 | 48 | 57.86 | 211 | 0.28 | 1.33 | 195 | 0.12 | 0.61 | 44.9 |

TABLE 4-continued

Measured dimensions, density and calculated porosity of composite samples.

| | Experimental conditions | | | Initial Dimensions | | | Final Dimensions | | | |
|---|---|---|---|---|---|---|---|---|---|---|
| Sample No. | Temp ° C. | Time h | % Extraction | Volume mm³ | Weight g | Density g/cm³ | Volume mm³ | Weight g | Density g/cm' | Estimated Porosity % |
| 10 | 50 | 54 | 58.12 | 214 | 0.26 | 1.21 | 255 | 0.11 | 0.45 | 59.3 |
| 15 | 50 | 48 | 53.75 | 309.2 | 0.36 | 1.16 | 329 | 0.17 | 0.50 | 54.2 |
| 22 | 60 | 24 | 65.35 | 6816 | 8.10 | 1.19 | 8705 | 2.81 | 0.32 | 70.70 |

Base density = 1.1 g/cm³

The morphology of the prepared samples was studied using Scanning Electron Microscope (SEM). Samples of both parallel planes (transverse) and perpendicular planes (longitudinal) were studied. Illustrative SEM images are shown in FIGS. 1-4 and described below.

Figure 4:
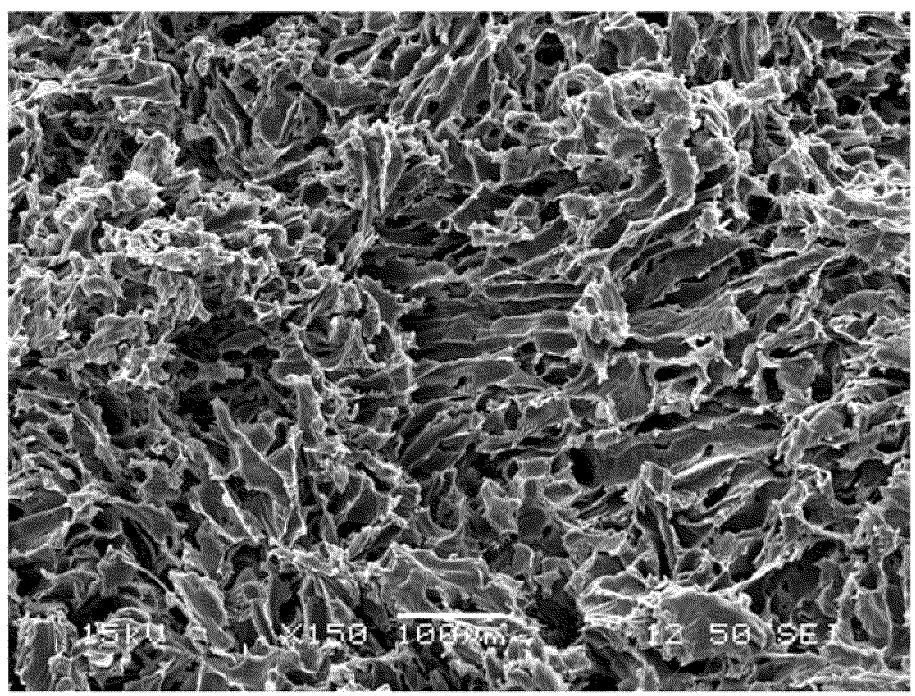
FIG. 4 shows an SEM image of an illustrative embodiment of a composite of the present technology, which includes PCL/sugar/PVA fibers in a weight ratio of 40/10/50, after extraction at 50° C.

FIG. 1 shows an SEM image of sample 7, which includes PCL/PEO/PVA fibers in a ratio of 40/15/45, after extraction at 40° C. The channel-like configuration in the sample is clearly visible. FIG. 2 shows an SEM image of sample 24, which includes PCL/PVA fibers in a ratio of 40/60, after extraction at 50° C. The channels are less visible for this sample presumably due to the higher concentration of fibers used, which probably allows pervasive erosion of the channels by water. FIG. 3 shows an SEM image of sample 18, a comparative sample, which includes PCL/Sugar in a ratio of 40/60, after extraction at 50° C. Since only sugar is present as the soluble material, the composite shows sphere-like openings instead of channels, as a result of which there is very poor interconnectivity in the composite. FIG. 4 shows an SEM image of sample 19, which includes PCL/Sugar/PVA fibers in a ratio of 40/10/50, after extraction at 50° C. The channel-like configuration is clearly visible thereby proving that a small amount of non-fibrous soluble agent can aid the fibers in developing even more defined channel structure.

Figure 5:
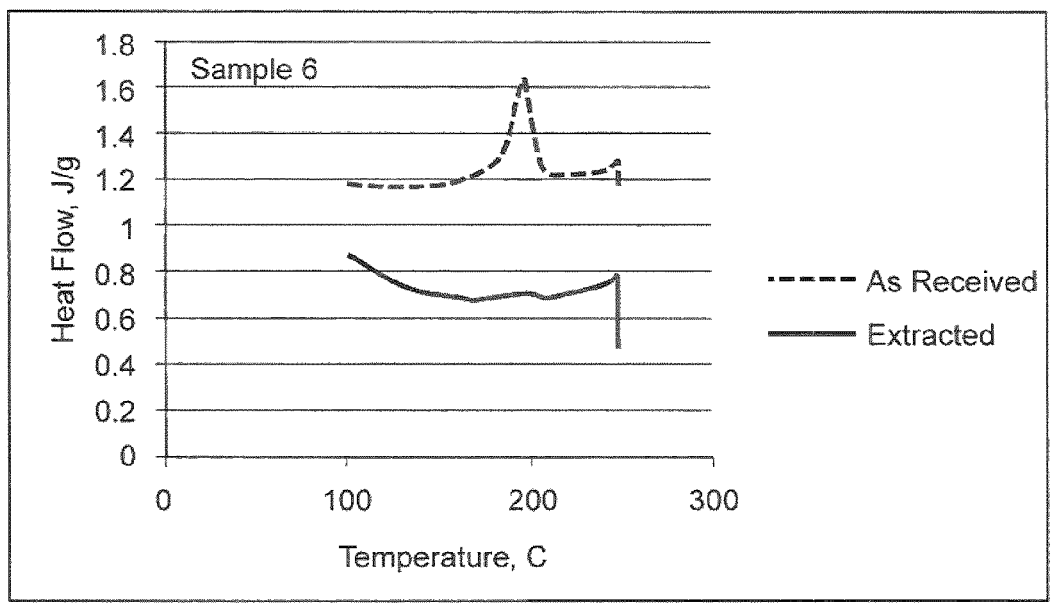
FIG. 5 is a graph of heat flow vs. temperature for PVA fibers in an illustrative embodiment of a composite of the present technology, which includes PCL/PEO/PVA fibers in a weight ratio of 30/30/40, after extraction at 40° C.
Figure 6:
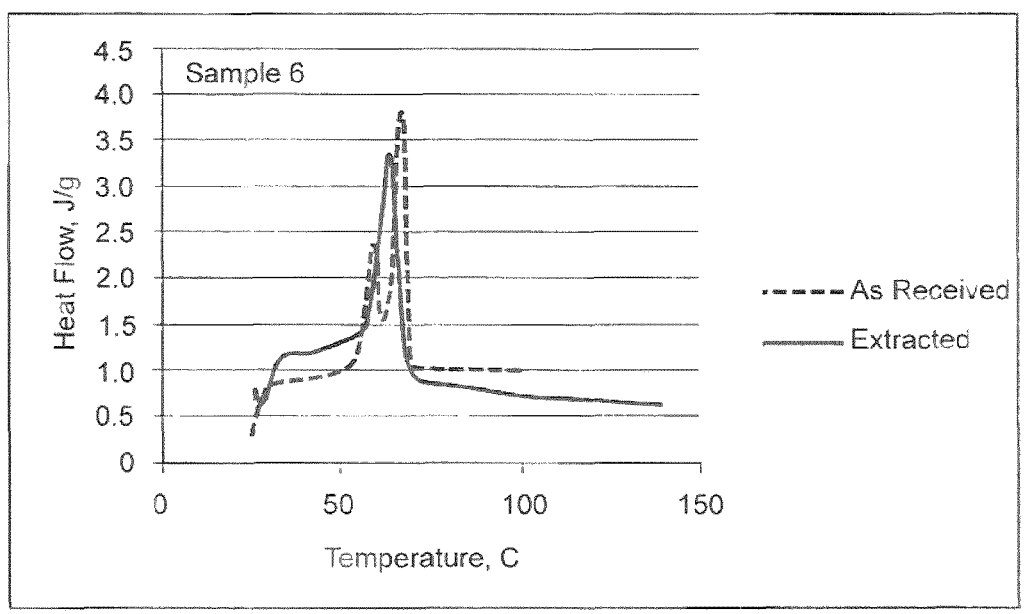
FIG. 6 is a graph of heat flow vs. temperature for PCL and PEO in an illustrative embodiment of a composite of the present technology, which includes PCL/PEO/PVA fibers in a weight ratio of 30/30/40, after extraction at 40° C.

Thermal properties of the materials used and the samples prepared were studied using Differential Scanning calorimetry (DSC). Samples of polymeric matrix material, fibers and additives were tested as received using Perkin Elmer Instrument, Model No. DSC-7. All samples were run under nitrogen. For initial characterization of samples, the program included: (a) heating from 25 to 200° C. using a ramp of 20° C./min, (b) holding the sample for 1 minute at 200° C., (c) cooling from 200 to 25° C. using a ramp of 10° C./min, (d) holding the sample for 2 minutes at 25° C., (e) rerunning steps (a) through (c). For PVA fibers, the program included: (a) heating from 25 to 250° C. using a ramp of 20° C./min, (b) holding the sample for 1 minute at 250° C., (c) cooling from 250 to 25° C. using a ramp of 10° C./min, (d) holding the sample for 2 minutes at 25° C., (e) rerunning steps (a) through (c). The different transitions for both the starting materials and the product composites were determined and comparative relative plots were plotted. Illustrative plots are shown in FIGS. 5-7. FIG. 5 illustrates the DSC curves of heat-flow-vs-temperature for PVA fibers as received, as well as in sample 6, which includes PCL/PEO/PVA fibers in a ratio of 30/30/40, after extraction at 40° C. The extracted sample shows only a minimum amount of PVA left behind in the sample. FIG. 6 illustrates the DSC curves of heat-flow-vs-temperature for PCL and PEO as received, as well as in sample 6, which includes PCL/PEO/PVA fibers in a ratio of 30/30/40, after extraction at 40° C. The "as received" samples show two peaks characteristic of PCL (lower temperature peak) and PEO (higher temperature peak), whereas the extracted sample displays a single peak which relates, most likely, only to PCL melting after being annealed.

EQUIVALENTS

The embodiments, illustratively described herein, may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like, include the number recited and refer to ranges which can be subsequently broken down into subranges as discussed above. Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A composite comprising:
   water-soluble polymeric fibers dispersed in a biodegradable polymer matrix using melt-processing such that a majority of the water-soluble polymeric fibers are in contact with other of the water-soluble polymeric fibers,
   a plurality of the water-soluble polymeric fibers contact a surface of the biodegradable polymer matrix, wherein the composite, when exposed to water or an aqueous solution, provides a porous biodegradable polymer matrix having a network of interconnected internal pores, wherein the interconnected internal pores are surface coated with a hydrophilic polymer; and
   a water-soluble polymeric additive that is immiscible with the biodegradable polymer matrix,
   wherein the biodegradable polymer matrix, the water-soluble polymeric fibers, and the water-soluble polymeric additive are present in a ratio of about 40/15/45, respectively.

2. The composite of claim 1, wherein the water-soluble polymeric fibers comprise poly(vinyl alcohol), poly(vinyl pyrrolidone), or polyethylene oxide.

3. The composite of claim 1, wherein the water-soluble polymeric fibers are at least 95% soluble when 1 gram of the water-soluble polymeric fibers is kept in 100 mL of water, for at least 30 minutes at a temperature of about 60° C.

4. The composite of claim 1, wherein the water-soluble polymeric fibers have a melting point which is above a melt-processing temperature or an extrusion temperature used during preparation of the composite.

5. The composite of claim 1, wherein the water-soluble polymeric fibers have an average diameter of about 0.1 µm to about 200 µm.

6. The composite of claim 1, wherein the water-soluble polymeric fibers have an average diameter of about 1 µm to about 50 µm.

7. The composite of claim 1, wherein the water-soluble polymeric fibers have an average diameter of about 50 µm to about 200 µm.

8. The composite of claim 1, wherein the water-soluble polymeric fibers have a length greater than their diameter.

9. The composite of claim 1, wherein the water-soluble polymeric fibers have an average length greater than 0.05 mm.

10. The composite of claim 1, wherein the water-soluble polymeric fibers are arranged in a woven or non-woven pattern.

11. The composite of claim 10, wherein the non-woven pattern is a felt.

12. The composite of claim 1, wherein the water-soluble polymeric fibers comprise about 30 wt % to about 75 wt % of a total weight of the composite.

13. The composite of claim 2, wherein the water-soluble polymeric fibers comprise poly(vinyl alcohol) having partial hydrolysis.

14. The composite of claim 2, wherein the poly(vinyl alcohol) of the water-soluble polymeric fibers have an average molecular weight of about 26,000 to about 36,000.

15. The composite of claim 1, wherein the biodegradable polymer matrix comprises poly(lactic acid), poly(glycolic acid), poly(caprolactone), poly(lactic acid) copolymer, poly (glycolic acid) copolymer, poly(caprolactone) copolymer, or a mixture of any two or more thereof.

16. The composite of claim 1, wherein the water-soluble polymeric additive is polyethylene glycol, polyethylene oxide, polyvinylpyrrolidone, or poly(2-ethyl-2-oxazoline).

17. A method comprising:
    melt-processing a biodegradable polymer, water-soluble poly(vinyl alcohol) fibers, and one or more of water-soluble additives which are immiscible in the biodegradable polymer, to provide a composite in which the water-soluble poly(vinyl alcohol) fibers are dispersed throughout a matrix formed by the biodegradable polymer such that a majority of the water-soluble poly(vinyl alcohol) fibers are in contact with other fibers and a plurality of the water-soluble poly(vinyl alcohol) fibers contact a surface of the matrix, wherein the matrix, the water-soluble poly(vinyl alcohol) fibers, and one or more of water-soluble additives are present in a ratio of about 40/15/45, respectively;
    exposing the composite to water or an aqueous solution under continuous agitation for a time and at a temperature sufficient to provide a porous biodegradable polymer matrix having a network of interconnected internal pores; and
    coating a surface of the interconnected internal pores of the matrix with a hydrophilic polymer.

18. The method of claim 17, wherein the melt-processing is carried out at a temperature of about 40° C. to about 200° C.

19. The method of claim 17, wherein the poly(vinyl alcohol) fibers, biodegradable polymer, and the one or more of water-soluble additives are processed together in a batch melt mixer and are compression-molded or extruded as a film, a sheet, a yarn, a cylindrical strand or strands, a tube, or a sheet or film having a cylindrical shape.

20. The method of claim 17, wherein the poly(vinyl alcohol) fibers, biodegradable polymer, and the one or more of water-soluble additives are combined in an extruder and a resulting composite is extruded as a film, a sheet, a yarn, a cylindrical strand or strands, a tube, or a sheet or film having a cylindrical shape.

21. The method of claim 17, wherein the poly(vinyl alcohol) fibers are first formed into a woven or non-woven construct and the matrix is deposited on to the construct and subsequently melted, compressed and cooled to form a film, a sheet, a yarn, a cylindrical strand or strands, a tube, or a sheet or film having a cylindrical shape.

22. The method of claim 17, wherein the poly(vinyl alcohol) fibers are first formed into a woven or non-woven construct and placed in a mold, the biodegradable polymer is injected into the mold to form an injection-molded composite, and the injection-molded composite is subsequently cooled to form a film, a sheet, a yarn, a cylindrical strand or strands, a tube, or a sheet or film having a cylindrical shape.

23. A method comprising:
    exposing a composite to water or an aqueous solution under continuous agitation for a time and at a temperature sufficient to provide a porous biodegradable polymer matrix having a network of interconnected internal pores, wherein the composite comprises a water-soluble poly(vinyl alcohol) fiber dispersed in a biodegradable polymer matrix such that a majority of the water-soluble poly(vinyl alcohol) fibers are in contact with other water-soluble poly(vinyl alcohol) fibers and a plurality of the water-soluble poly(vinyl alcohol) fibers contact a surface of the biodegradable polymer matrix and one or more of water-soluble additives which are immiscible in the biodegradable polymer matrix, wherein the biodegradable polymer matrix, the water-soluble poly(vinyl alcohol) fiber, and the one or more of water-soluble additives are present in a ratio of about 40/15/45, respectively; and coating a surface of the interconnected internal pores of the porous biodegradable polymer matrix with a hydrophilic polymer.

24. The method of claim 23, wherein the temperature of the water or aqueous solution is about 30° C. to about 60° C.

25. The method of claim 23, wherein the hydrophilic polymer is selected from the group consisting of fibronectin, vitronectin, laminin, collagen, elastin, and combinations thereof.

26. The porous biodegradable polymer matrix formed by the method of claim 23.

* * * * *